United States Patent [19]

Salamon et al.

[11] Patent Number: 4,599,345
[45] Date of Patent: Jul. 8, 1986

[54] CHLOROMETHYL QUINOLINE DERIVATIVES AND USE THEREOF AS ANALGESICS

[75] Inventors: Zoltán Salamon; Ilona Imre née Virág, both of Tiszavasvari; Magdolna Sebestyén, Hajdunanas, all of Hungary

[73] Assignee: Alkaloide Vegyeszeti Gyar, Tiszavasvari, Hungary

[21] Appl. No.: 557,106

[22] Filed: Dec. 1, 1983

[30] Foreign Application Priority Data

Dec. 2, 1982 [HU] Hungary ................ 3869/82

[51] Int. Cl.$^4$ .................. A61K 31/47; C07D 215/12
[52] U.S. Cl. .................. 514/311; 546/180
[58] Field of Search .......... 546/180; 424/258; 514/311

[56] References Cited

U.S. PATENT DOCUMENTS 4,277,607 7/1981 Bulidon et al. ............ 546/180

FOREIGN PATENT DOCUMENTS 909080 10/1962 United Kingdom .

OTHER PUBLICATIONS

Kato et al., Chem. Ph. Bull., 29, 1069–1075, 1969.

Primary Examiner—Glennon H. Hollrah
Assistant Examiner—D. B. Springer
Attorney, Agent, or Firm—Karl F. Ross; Herbert Dubno

[57] ABSTRACT

A chlorinated quinoline derivative of formula (I)

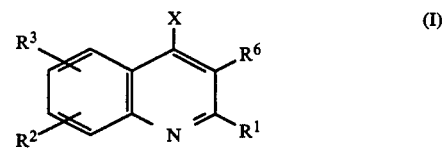

wherein $R^1$ is —$CCl_3$, —$CF_3$, —$CHCl_2$ or —$CH_2Cl$, $R^2$ is hydrogen when $R^3$ is not hydrogen, or is halogen, $C_{1-4}$ alkoxy, $C_{1-4}$ alkyl or $R^1$, $R^3$ is hydrogen when $R^2$ is not hydrogen or is halogen, $C_{1-4}$ alkyl, $C_{1-4}$ alkoxy or $CF_3$, $R^6$ is hydrogen or halogen, X is halogen. The compounds are made by chlorination of selected compounds as disclosed and the new compounds can have antimicrobial, antifungal or analgesic effects.

16 Claims, No Drawings

CHLOROMETHYL QUINOLINE DERIVATIVES AND USE THEREOF AS ANALGESICS

FIELD OF THE INVENTION

The invention relates to new chloromethyl quinoline derivatives of formula (I)

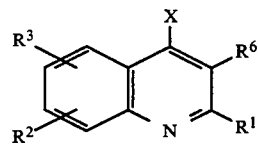

(I)

and the preparation thereof, wherein
$R^1$ is a —CCl$_3$, —CF$_3$, —CHCl$_2$ or —CH$_2$Cl group,
$R^2$ is hydrogen, halogen, $C_{1-4}$ alkoxy, $C_{1-4}$ alkyl or $R^1$
$R^3$ is hydrogen or halogen, $C_{1-4}$ alkyl, $C_{1-4}$ alkoxy or CF$_3$
$R^6$ is hydrogen or halogen,
X is halogen, preferably chlorine or bromine.

The compounds prepared according to the present invention are useful pharmaceutical products and intermediates in the preparation of pharmaceutical products and plant protectives.

BACKGROUND OF THE INVENTION

From the state of the art quinoline derivatives are known which are biologically active, for example they exert an antimalarial (J. Med. Chem. 14. 1221, 1971) or antibacterial effect (British patent specification No. 874,980). Among others these earlier references make the development of a broadly applicable method for the preparation of chloromethyl quinoline derivatives justified.

The method used up to now for this purpose (J. Chem. Soc. 123 2882, 1923) is suitable first of all for the preparation of 2-tribromo-methyl-quinoline derivatives (J. Chem. Soc. 1950 628; ibid 1951 1145; ibid 1953 1369) and may be applied for 4-chloro-quinaldine derivatives with a poor yield (J. Med. Chem. 14 1221, 1971).

According to a more advantageous method for the preparation of 2-trichloromethyl-4-chloro-quinoline, 4-quinaldinole was refluxed in the presence of phosphorus pentachloride in phosphoroxy chloride whereupon the product could be isolated from the obtained mixture by the aid of chromatography with a moderate yield (Chem. Ph. Bull 29 1069, 1981). Having condensed ethyl-trichloro-acetyl-acetate with the appropriate aniline, 2-trichloromethyl-4-quinolinole derivatives were obtained with a moderate yield (J. Org. Chem. 31 3369, 1966); there is no known process in the state of the art for the transformation of these compounds to 4-chloro derivatives.

A further disadvantage of the known methods besides the poor to moderate yields is the fact that they may be used only for the preparation of 2-chloromethyl-quinoline derivatives and the selectivity of the reactions is not always sufficient. In certain cases the starting substance (e.g. the trichloro-aceto-acetic ester) is difficult to obtain and is an expensive compound.

DESCRIPTION OF THE INVENTION

The present invention is based on the recognition that the alkyl group or groups of methyl-4-chloro-quinoline and methyl-4-oxy-quinoline may be selectively chlorinated.

For this purpose the phosphorus pentachloride or a form thereof formed "in situ" from phosphorus trichloride and chlorine gas are considered as suitable chlorinating agent.

In developing this process we surprisingly recognized that small quantities of phosphorus pentahalides or phosphorus trihalides in the presence of a solvent have a catalytic effect on the side-chain halogenation performed with chlorine, accelerating the reaction and increasing the selectivity thereof. Thus the di- and trihalogenation of the homoaromatic alkyl groups of quinoline becomes possible with good yields.

The compounds of formula (I) may be prepared as follows:

(a) chlorinating a quinoline derivative of formula (II)

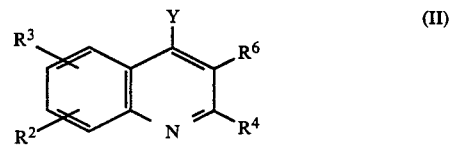

(II)

wherein
$R^2$, $R^3$ and $R^6$ are as defined above,
Y is halogen or a hydroxyl group,
$R^4$ stands for a methyl, —CH$_2$Cl or —CHCl$_2$-group, or (b) chlorinating a quinoline derivative of formula (III)

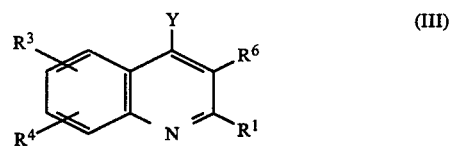

(III)

wherein
$R^1$, $R^3$, $R^4$, Y and $R^6$ are as defined above, or (c) chlorinating a quinoline derivative of formula (IV)

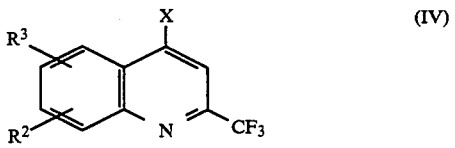

(IV)

wherein
X, $R^2$, $R^3$ are as defined above, or (d) chlorinating a quinoline derivative of formula (V)

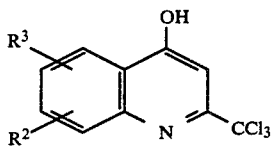

wherein
R² and R³ are as defined above.

In addition to the above substituents the following are mentioned in the specification:

R⁵ which can be —CCl₃, —CHCl₂ or a —CH₂Cl group, and

R⁷ which can be —CH₃, —CHCl₂, —CH₂Cl or a —CF₃ group.

The meaning of R¹ to R⁷, X and Y does not change in the specification and therefore will not be repeated.

Thus according to an advantageous procedure of the process variant (a) and (b) of the present invention, phosphorus pentachloride or phosphoroxy chloride and phosphorus pentachloride or chlorine gas or phosphoroxy chloride and chlorine gas may be used as chlorinating agent.

It depends on the desired endproducts which reaction conditions are chosen. Thus by the aid of the above procedures, the compounds of formula (VI)

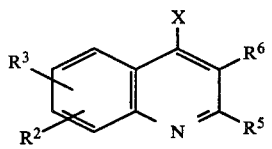

which belong under formula (I), may be advantageously prepared if quinoline derivatives of formula (II) are chlorinated at a temperature of 70° to 140° C. in the presence of halogenated hydrocarbon or phosphoroxy chloride as solvent.

If compounds of formula (VII)

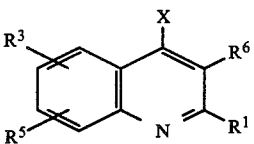

which fall under formula (I), are to be prepared, a compound of formula (III) is chlorinated with phosphorus trihalide and chlorine gas preferably at a temperature of 150° to 220° C. in the presence of halogenated hydrocarbon as solvent optionally under pressure.

For the above two process varients, mono-, di- or trichlorinebenzene or carbon tetrachloride may be used as solvent.

If the desired compounds fall under the formula (VIII)

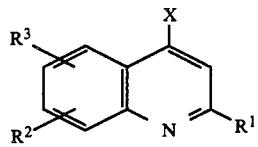

which belong under formula (I), a compound of formula (IX)

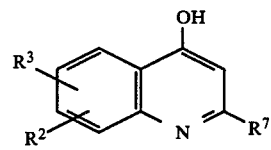

is chlorinated with phosphorus pentachloride at a temperature of 120° to 150° C., preferably in the presence of halogenated hydrocarbon. In this case, too, it is advantageous to use the chlorinated benzenes as solvent.

According to process varient (c) of the invention, quinoline derivatives of formula (XI),

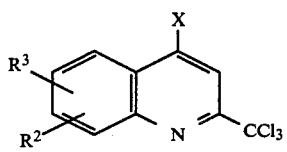

representing a subcase of the compounds of formula (I), may be advantageously prepared. In this case a quinoline derivative of formula (IV) is reacted with aluminum chloride preferably in the presence of a solvent as carbon disulfide, nitrobenzene or acetylchloride.

Process variant (d) according to the invention is advantageous for the preparation of compounds of formula (XII),

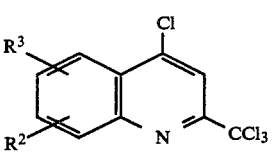

which belongs under formula (I). In this case a compound of formula (V) is reacted with phosphoroxy chloride but may be chlorinated with phosphorus pentachloride, too, at a temperature of 20° to 100° C.

According to process variant (d) quinoline derivatives of formula (XIII)

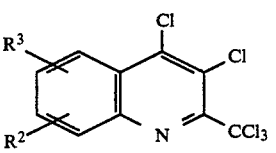

may be advantageously prepared by reacting a compound of formula (V) at a temperature of 110° to 150° C. with phosphorus pentachloride in the presence of a solvent such as a chlorinated hydrocarbon, preferably chlorinated benzene.

The chlorinated quinoline derivatives of formula (I) are new where $R^1$ and $R^3$ are not simultaneously hydrogen.

The quinoline derivatives of formula (I) may be used for the synthesis of pharmaceutical products and plant-protecting agents.

The quinoline derivatives used as starting material in the reactions were prepared by methods generally known from the state of art. Thus the 2-methyl-4-oxy-quinoline derivatives were prepared by the Conrad-Limpach synthesis modified by Hauser-Reynold (J. Am. Chem. Soc. 70 2402, 1948) while the appropriate 2-trifluoromethyl-4-quinoline was synthesized by the method indicated by A. S. Dey; M. M. Joullie (J. Het. Chem. 2 113, 1965). From this the appropriate 2-trifluoromethyl-4-halo derivative heated in phosphoroxy halide was obtained.

SPECIFIC EXAMPLES

The details of the present process are demonstrated with the help of the following examples.

EXAMPLE 1

2-Trichloromethyl-4,8-dichloroquinoline

The mixture of 1.9 g of 2-methyl-8-chloro-4-quinolinole and 9.0 g of phosphorus pentachloride is heated in 20 ml of monochlorobenzene to 130° to 135° C. and stirred at this temperature for 2 hours. The reaction mixture is evaporated in vacuo, the residue is crystallized from 20 ml of methanol.

Yield: 2.01 g, 64.5%.

EXAMPLE 2

2-Trichloromethyl-6-methyl-4-chloroquinoline

The mixture of 1.9 g of 2,6-dimethyl-4-chloro-quinoline and 6.5 g of phosphorus pentachloride is heated in 20 ml of phosphoroxy chloride for 3 hours, then the mixture is admixed with ice water and the separated product is filtered.

Yield: 2.81 g; 95.1%.

EXAMPLE 3

2-Trichloromethyl-8-trifluoromethyl-4-chloro-quinoline 14.5 g of 2-methyl-8-trifluoromethyl-4-quinolinole are refluxed in 70 ml of phosphoroxy chloride for 20 minutes under stirring. The mixture is cooled to 70° C., 10 ml of $PCl_3$ are added and chlorine gas is bubbled through the mixture at reduced pressure, the residue is treated with ice water and the separated product is filtered.

Yield: 22.1 g; 99.1%.

EXAMPLE 4

2-Monochloromethyl-8-methyl-4-chloro-quinoline and 2-dichloromethyl-8-methyl-4-chloro-quinoline The mixture of 1.9 g of 2,8-dimethyl-4-chloroquinoline and 2.1 g of phosphorus pentachloride is refluxed in 5 ml of carbon tetrachloride under stirring for 2.5 hours. It is cooled to room temperature and after standing for a night the separated crystals are filtered. It consists of the starting material (30 mole %) and the hydrochloride salt of 2-monochloromethyl-8-methyl-4-chloroquinoline (25 mole %). The filtrate is evaporated in vacuo, the residue is treated by column-chromatography (silica gel, eluent: cyclohexane).

In the first fraction 2-trichloromethyl-8-methyl-4-chloro-quinoline (10 mole %), then 2-dichloromethyl-8-methyl-4-chloro-quinoline is eluted (23 mole %). Finally 2-monochloromethyl-8-methyl-4-chloro-quinoline (10 mole %) is obtained.

EXAMPLE 5

2-Trichloromethyl-8-monochloromethyl-4-chloro-quinoline

A mixture of 1.92 g of 2,8-dimethyl-4-chloro-quinoline and 15 ml of monochlorobenzene and 12.5 g of phosphorus pentachloride is refluxed for 100 hours under stirring. Isolation is carried out as in Example 1.

Yield: 2.3 g; 69.7%.

EXAMPLE 6

2-Trichloromethyl-4,6,8-trichloro-quinoline 24.8 g of 2-methyl-4,6,8-trichloro-quinoline are dissolved in 100 ml of monochlorobenzene and the mixture is heated to 80° C. 1 ml of phosphorus tribromide is added and under intensive stirring chlorine gas is bubbled through the system and heated to 100° C. and the mixture is stirred at this temperature for 2 hours. It is evaporated in vacuo, the residue is treated according to Example 1.

Yield: 31.1 g; 92.1%.

EXAMPLE 7

2-Trichloromethyl-8-trifluoromethyl-4-bromo-quinoline 3.4 g of 2,8-bis-(trifluoromethyl)-4-bromo-quinoline, 1.5 g of freshly sublimated aluminum-chloride are allowed to stand in 30 ml of abs. carbon disulfide for a night at room temperature. The organic phase is washed with 50 ml of 10 percent icy hydrochloric acid, 2×50 ml of water, dried and evaporated. The residue is recrystallized from aqueous methanol.

Yield: 3.3 g; 86.9%.

EXAMPLE 8

2-Trichloromethyl-8-dichloromethyl-4-chloro-quinoline

A mixture of 1.92 g of 2,8-dimethyl-4-chloro-quinoline and 15.0 g of phosphorus pentachloride is kept in 100 ml of o-dichlorobenzene at a temperature of 175° C. for 4 hours. Meanwhile the phosphorus trichloride formed in the reaction is continuously distilled off. The reaction mixture is treated as described in Example 1.

Yield: 3.1 g; 85.2%.

EXAMPLE 9

2,6-bis-(Trichloromethyl)-4-chloro-quinoline 8.66 g of 2,6-dimethyl-4-oxy-quinoline are refluxed in 30 ml of phosphoroxy chloride for 30 minutes, the reaction mixture is cooled to 70° C. and hexane is added. The precipitated 2,6-dimethyl-4-chloro-quinoline hydrochloride salt crystals are filtered off and triturated with ice acetone and carbon tetrachloride. The obtained substance is kept over 75 g of phosphorus pentachloride at a temperature of 180° C. for 18 hours. The obtained melt is treated in the usual manner.

Yield: 9.7 g; 48.7%.

EXAMPLE 10

29.5 g of 2-trichloromethyl-6-methyl-4-chloro-quinoline are dissolved in 100 ml of 1,2,4-trichlorobenzene, 0.5 ml of phosphorus tribromide is added and under stirring the mixture is heated and when an inner temperature of 100° C. is attained a strong chlorine gas current is passed through the reaction mixture. It is further heated to 200° C. and chlorinated at this temperature for 2 hours. The reaction mixture is treated as described in Example 12.

Yield: 36.3 g; 91.2%.

EXAMPLE 11

2,8-bis-(Trichloromethyl)-4-chloro-quinoline 233 ml of carbon tetrachloride and 80 ml of phosphorus trichloride are given into a stirring double-wall Hastelay-C-autoclave of a volume of 1 liter. At 80° C. 55 g of chlorine gas are absorbed in the mixture, it is stirred for half an hour and 17.3 g of 2,8-dimethyl-4-quinolinole are added. The temperature of the reaction mixture is slowly raised to 180° C. and stirred at this temperature for 24 hours. Meanwhile the inner pressure is raised to 28–29 atmospheres. The solvent is distilled off and the distillation residue is treated as described in Example 1.

Yield: 33.2 g; 83.4%.

EXAMPLE 12

47.9 g of 2,8-dimethyl-4-chloro-quinoline are heated in 200 ml of 1,2,4-trichlorobenzene to 95° C. 1 ml of phosphorus tribromide is added and chlorine gas is passed through the mixture under intensive stirring. It is allowed to heat to 130° C., kept at this temperature for 15 minutes and then for further 4 hours at 200° C. The solvent is distilled off in vacuo and the residue is crystallized from 400 ml of ethanol.

Yield: 85.6 g; 85.8%.

EXAMPLE 13

2-Trichloromethyl-4,6-dichloro-quinoline 3.0 g of 2-trichloromethyl-6-chloro-4-quinoline are refluxed in 20 ml of phosphoroxy chloride for 3 hours. At reduced pressure the reaction mixture is evaporated, the residue is treated in the usual manner.

Yield: 2.2 g; 69.8%.

EXAMPLE 14

2-Dichloromethyl-5-methyl-3,4-dichloro-quinoline 1.73 g of 2,5-dimethyl-4-quinolinole are added to the 120°–125° C. mixture of 20 ml of monochlorobenzene and 8.8 g of phosphorus pentachloride in small portions. After the addition the mixture is stirred at this temperature still for one hour and treated as described in Example 1.

Yield: 2.1 g; 71.2%.

EXAMPLE 15

2-Trichloromethyl-3,4,6-trichloro-quinoline 1.94 g of 2-methyl-6-chloro-4-quinolinole are reacted with 12.0 g of phosphorus pentachloride according to Example 14.

Yield: 2.5 g; 71.4%.

EXAMPLE 16

2,2'-bis-(Trichloromethyl)-4,4'-dichloro-6,6'-biquinoline

A mixture of 1.5 g of 2,2'-dimethyl-4,4'-dichloro-6,6'-biquinoline, 9.0 g of phosphorus pentachloride, 25.0 ml of monochlorobenzene is refluxed for 1 hour. It is evaporated in vacuo, the residue is treated with 20 ml of cold methanol and crystallized.

Yield: 1.8 g; 64.3%.

| | Compound | Method, number according to the example: | Yield: (%) |
|---|---|---|---|
| 17 | 2-Trichloromethyl-4-chloroquinoline | 1 | 73.4 |
| 18 | 2-Trichloromethyl-4-chloroquinoline | 2 | 59.3 |
| 19 | 2-Trichloromethyl-3,4-dichloro-quinoline | 15 | 67.1 |
| 20 | 2-Trichloromethyl-5-methyl-4-chloro-quinoline | 1 | 74.7 |
| 21 | 2-Trichloromethyl-3,4-dichloro-5-methyl-quinoline | 15 | 61.5 |
| 22 | 2-Trichloromethyl-6-methyl-4-chloro-quinoline | 1 | 57.3 |
| 23 | 2-Trichloromethyl-3,4-dichloro-6-methyl-quinoline | 15 | 73.5 |
| 24 | 2-Dichloromethyl-3,4-dichloro-6-methyl-quinoline | 14 | 66.3 |
| 25 | 2-Trichloromethyl-8-methyl-4-chloro-quinoline | 2 | 87.3 |
| 26 | 2-Trichloromethyl-4,5-dichloro-8-methyl-quinoline | 1 | 81.8 |
| 27 | 2-Trichloromethyl-4,6-dichloro-quinoline | 1 | 83.9 |
| 28 | 2-Dichloromethyl-3,4,6-trichloro-quinoline | 14 | 75.2 |
| 29 | 2-Trichloromethyl-4,7-dichloro-quinoline | 1 | 63.4 |
| 30 | 2-Trichloromethyl-3,4,7-trichloro-quinoline | 15 | 72.7 |
| 31 | 2-Trichloromethyl-4,6,8-trichloro-quinoline | 1 | 70.6 |
| 32 | 2-Trichloromethyl-4,6,8-trichloro-quinoline | 2 | 96.7 |
| 33 | 2-Trichloromethyl-6-methoxy-4-chloro-quinoline | 1 | 64.3 |
| 34 | 2-Trichloromethyl-6-methoxy-4-chloro-quinoline | 2 | 69.9 |
| 35 | 2-Trichloromethyl-6-methoxy-3,4-dichloro-quinoline | 15 | 43.5 |
| 36 | 2-Trichloromethyl-8-methoxy-4-chloro quinoline | 1 | 48.2 |
| 37 | 2-Trichloromethyl-6-trifluoromethyl-4-chloro-quinoline | 2 | 94.3 |
| 38 | 2-Trichloromethyl-6- | 7 | 73.7 |

| Compound | Method, number according to the example: | Yield: (%) |
|---|---|---|
| trifluoromethyl-4-chloro-quinoline | | |
| 39 2-Trichloromethyl-7-trifluoromethyl-4-chloro-quinoline | 2 | 79.8 |
| 40 2-Trichloromethyl-7-trifluoromethyl-4-chloro-quinoline | 7 | 84.5 |
| 41 2-Trichloromethyl-8-trifluoromethyl-4-chloro-quinoline | 2 | 87.5 |
| 42 2-Trichloromethyl-8-trifluoromethyl-4-chloro-quinoline | 1 | 71.4 |
| 43 2-Trichloromethyl-8-trifluoromethyl-4-chloro-quinoline | 7 | 78.3 |
| 44 2,6-bis-(Trichloromethyl)-4-chloro-quinoline | 12 | 87.6 |
| 45 2,2'-bis-Trichloromethyl-8,8'-dimethyl-4,4'-dichloro-6,6'-biquinoline | 16 | 73.4 |
| 46 2-Trifluoromethyl-4-chloro-5-dichloromethyl-quinoline | 10 | 73.2 |
| 47 2-Trifluoromethyl-4-chloro-6-trichloromethyl-quinoline | 10 | 87.4 |
| 48 2-Trifluoromethyl-4-chloro-7-trichloromethyl-quinoline | 10 | 81.7 |
| 49 2-Trifluoromethyl-4-chloro-8-dichloromethyl-quinoline | 10 | 79.3 |
| 50 2-Trifluoromethyl-4,5-dichloro-8-trichloromethyl-quinoline | 10 | 84.6 |
| 51 2-Trifluoromethyl-4-chloro-8-trichloromethyl-quinoline | 10 | 67.3 |
| 52 2-Trichloromethyl-4-chloro-7-methyl-quinoline | 1 | 73.2 |
| 53 2-Trichloromethyl-4-chloro-5-trifluoromethyl-quinoline | 1 | 80.3 |
| 54 2-Trichloromethyl-4,5,7-trichloro-quinoline | 1 | 87.3 |
| 55 2-Trichloromethyl-4,7,8-trichloro-quinoline | 1 | 72.1 |
| 56 2-Trichloromethyl-4,6-dichloro-8-methyl-quinoline | 1 | 86.3 |
| 57 2-Trichloromethyl-4,7-dichloro-8-methyl-quinoline | 1 | 93.4 |
| 58 2-Trichloromethyl-4,5,8-trichloro-quinoline | 1 | 92.7 |
| 59 2-Trichloromethyl-4,8-dichloro-6-methyl-quinoline | 1 | 73.7 |
| 60 2-dichloromethyl-4,8-dichloro-6-methyl-quinoline | 14 | 65.3 |

| NMR data and melting point values of the compounds prepared according to the examples | | | | | | |
|---|---|---|---|---|---|---|
| $R^1$ | $R^6$ | X | $R^3$ | $R^2$ | m.p. (°C.) | $^1$H—NMR data (ppm) |
| $CCl_3$ | H | Cl | H | H | 64–65 | 8.28 dd ($J^3$ 9.0Hz; $J^4$ 1.5 Hz 1H) and 8.22 dd ($J^3$ 7.0 Hz; $J^4$ 1.5 Hz 1H) H (7 and 8) 8.16 s(1H), H(3) 7.86 ddd ($J^3$ 7.0 Hz; $J^{3'}$ 9.0 Hz; $J^4$: 1.5 Hz 1H) and 7.74 ddd ($J^3$ 9.0 Hz; $J^{3'}$ 9.0 Hz; $J^4$: 1.5 Hz 1H) H (6 and 7) |
| $CCl_3$ | Cl | Cl | H | H | 130–133 | 8.27 dd ($J^3$ 8.0 Hz; $J^4$ 2.0 Hz 1H) and 8.23 dd ($J^3$ 8.0 Hz; $J^4$ 2.0 Hz 1H) H (5 and 8) 7.87 ddd ($J^3$ 8.0 Hz; $J^{3'}$ 7.0 Hz; 7.0 Hz 1H) and 7.77 ddd ($J^3$ 8.0 Hz; $J^{3'}$ 7.0 Hz; $J^4$ 7.0 Hz 1H) H (6 and 7) |
| $CCl_3$ | H | Cl | 5Me | H | 89–92 | 8.10 s (1H) H (3); 3.02 s (3H) methyl (5), 8.07 dd (1H); 7.70 dd (1H); 7.47 dd (1H); H (6-, 7 and 8) |
| $CCl_3$ | Cl | Cl | 5Me | H | 172–174 | 8.06 dd ($J^3$ 8.5 Hz; $J^4$ 1Hz 1H) and 7.56 dd ($J^3$ 8.0 Hz; $J^4$ 1Hz 1H) H (6 and 8) 7.66 dd ($J^3$ 8.5 Hz; $J^{3'}$ 8.0 Hz) H (7) 3.05 s (3H) methyl (5). |
| $CHCl_2$ | Cl | Cl | 5Me | H | 140–142.5 | 8.07 dd (1H) and 7.47 dd (1H) H (6 and 8); 7.60 dd (1H) H (7); 7.30 s (1H) dichloromethyl H (2); 3.10 s (3H) methyl (5). |
| $CCl_3$ | H | Cl | 6Me | H | 85–88 | 8.12 s (1H) H (3); 8.10 d ($J^3$ 8.5 Hz, 1H) H (8); 8.00 dq ($J^4$ 0.9 Hz; $J^{4'}$ 2.0 Hz 1H) H (5); 7.70 dd ($J^3$ 8.5 Hz; $J^4$ 2.0 Hz 1H) H (7); 2.60 s (b) methyl (6). |
| $CCl_3$ | Cl | Cl | 6Me | H | 155–157 | 8.08 d ($J^3$ 8.0 Hz, 1H) H (8); 8.00 m (b) (1H) H (5); 7.67 dd ($J^3$ 8pHz, $J^4$ 2.0 Hz 1H) H (7); 2.65 s (3H) methyl (6). |
| $CHCl_2$ | Cl | Cl | 6Me | H | 96–99 | 8.05 d ($J^3$ 8 Hz 1H) H (8); 7.90 m (1H) H (5); 7.61 dd ($J^3$ 8.0 Hz, $J^4$ 1.9 Hz, 1H) H (7); 7.30 s (1H) dichloromethyl H (2); 2.60 s (3H) methyl (6). |
| $CCl_3$ | H | Cl | 7Me | H | 82–83 | 8.13 d ($J^3$ 8.5 Hz 1H) H (5); 8.09 s (1H) H (3); 8.00 s (b) (1H) H (8); 7.57 dd ($J^3$ 8.5 Hz, $J^4$ 1.5 Hz 1H) H (6); 2.61 s (3H) methyl (7). |
| R | R | X | R | R | m.p. (°C.) | $^1$H—NMR data (ppm) |
| $CCl_3$ | H | Cl | 8Me | H | 104–106 | 8.14 s (1H) H (3); 8.08 dd ($J^3$ 8.5 Hz; $J^4$ 1.5 Hz, 1H) H (5); 7.68 dm (1H) H (7); 7.60 dd ($J^3$ 8.5 Hz; $J^{3'}$ 2.5 Hz; 1H) H (6); 2.87 s (3H) methyl (8). |
| $CHCl_2$ | H | Cl | 8Me | H | 104–107 | 8.10 dd ($J^3$ 8.0 Hz, $J^4$ 0.9 Hz, 1H ) H (5); 7.97 s (1H) H (3); 7.60 dd ($J^3$ 8.0 Hz; $J^{3'}$ 7.6 Hz, 1H) H (6); 7.66 dm ($J^3$ 7.6 Hz, 1H) H (7), 6.85 s (1H) dichloromethyl H (2); 2.75 s (3H) methyl (8). |
| $CH_2Cl$ | H | Cl | 8Me | H | 69–72 | 8.08 dd (1H) H (5); 7.70 s (1H) H (3); |

-continued

NMR data and melting point values of the compounds prepared according to the examples

| | | | | | |
|---|---|---|---|---|---|
| CCl$_3$ | H | Cl | 5CF$_3$ | H | 44–45 | 7.62 d (1H) H (7); 7.52 dd (1H) H (6); 4.85 s (2H) chloromethyl H; 2.80 s (3H) methyl (8) 8.44 dd (J$^3$ 9.0 Hz, J$^4$ 1 Hz, 1H) H (8); 8.31 s (1H) H (3); 8.23 d (b) (J$^3$ 7.5 Hz, 1H) H (6); 7.87 dd (J$^3$ 9.0 Hz, J$^{3'}$ 7.5 Hz, 1H) H (7). |

| R$^1$ | R$^6$ | X | R$^3$ | R$^2$ | m.p. (°C.) | $^1$H—NMR data (ppm) |
|---|---|---|---|---|---|---|
| CCl$_3$ | H | Cl | 6CF$_3$ | H | 47–48 | 8.56 dq (J$^4$ 2.0 Hz; J$^4_{F-H}$ 0.9 Hz, 1H) H (5); 8.35 dq (J$^3$ 9.0 Hz, J$^5_{F-H}$ 0.6 Hz, 1H) H (8); 8.25 s (1H) H (3); 8.03 dd (b) (J$^3$ 9.0 Hz; J$^4$ 7.0 Hz, 1H) H (7). |
| CCl$_3$ | H | Cl | 7CF$_3$ | H | 72–74 | 8.55 dq (J$^4$ 1.8 Hz; J$^4_{F-H}$ 0.9 Hz, 1H) H (8); 8.39 dq (J$^3$ 9.0 Hz; J$^5_{F-H}$ 0.8 Hz, 1H) H (5); 8.27 s (1H) H (3); 7.96 dd (b) (J$^3$ 9.0 Hz; J$^4$ 1.8 Hz 1H) H (6). |
| CCl$_3$ | H | Cl | H | 8CF$_3$ | 88–90 | 8.50 dd (J$^3$ 8.5 Hz; J$^4$ 1.5 Hz, 1H) H (5); 8.28 s (1H) H (3); 8.24 d(b) (J$^3$ 8.5 Hz, 1H) H (7); 7.85 dd (J$^3$ 8.5 Hz; J$^{3'}$: 8.5 Hz 1H) H (6). |
| CCl$_3$ | H | Cl | H | 6Cl | 99–101 | 8.24 d (j$^4$ 2.0 Hz; 1H) H (5); 8.18 s (1H) H (3); 8.17 d (J$^3$ 8.5 Hz; 1H) H (8); 7.78 dd (J$^3$ 8.5 Hz J$^4$ 2.0 Hz; 1H) H (7). |
| CCl$_3$ | Cl | Cl | H | 6Cl | 166–169 | 8.25 dd (J$^4$ 2.0 Hz; 0.5 Hz; 1H) H (5); 8.15 dd (J$^3$ 9.0 Hz; J$^5$ 0.5 Hz 1H) H (8); 7.77 dd (J$^3$ 9.0 Hz; J$^4$ 2.0 Hz 1H) H (7). |
| CHCl$_2$ | Cl | Cl | H | 6Cl | 90–92 | 8.13 d (j$^4$ 1.5 Hz; 1H) H (5); 8.10 d (J$^3$ 7.2 Hz, 1H) H (8); 7.72 dd (J$^3$ 7.2 Hz; J$^4$ 1.5 Hz 1H) H (7); 7.35 s (1H) 2-dichloromethyl H. |
| CCl$_3$ | H | Cl | H | 7Cl | 82–84 | 8.25 dd (J$^4$ 2.0 Hz; J$^5$ 0.4 Hz; 1H) H (8); 8.20 d (b) (J$^3$ 9.0 Hz 1H) H (5); 8.15 s (1H) H (3); 7.69 dd (J$^3$ 9.0 Hz; J$^4$ 2.0 Hz; 1H) H (6). |
| CCl$_3$ | Cl | Cl | H | 7Cl | 144–146 | 8.23 d (J$^4$ 2.0 Hz, 1H) H (8); 8.14 d (J$^3$ 9.0 Hz; 1H) H (5); 7.72 dd (J$^3$ 9.0 Hz; J$^4$ 2 Hz; 1H) H (7). |
| CCl$_3$ | H | Cl | H | 8Cl | 126–128 | 8.22 s (1H) H (3); 8.18 dd (J$^3$ 8.7 Hz; J$^4$ 1.5 Hz) H (5); 7.99 dd (J$^3$ 7.8 Hz; J$^4$ 1.5 Hz; 1H) H (7) 7.65 dd (J$^3$ 8.7 Hz; J$^{3'}$ 7.8 Hz 1H) H (6). |

| R | R | X | R | R | m.p. (°C.) | $^1$H—NMR data (ppm) |
|---|---|---|---|---|---|---|
| CCl$_3$ | Cl | Cl | H | 6MeO | 134–136 | 8.06 d (J$^3$ 9.0 Hz; 1H) H (8); 7.45 dd (J$^3$ 9.0 Hz, J$^4$ 2.2 Hz; 1H) H (7); 7.40 d (J$^4$ 2.2 Hz; 1H) H (5). |
| CCl$_3$ | H | Cl | H | 8MeO | 148–151 | 8.18 s (1H) H (3); 7.81 dd (J$^3$ 8.85 Hz; J$^4$ 1.3 Hz, 1H) H (5); 7.65 dd (J$^3$ 8.85 Hz; J$^3$ 7.75 Hz, 1H) H (6):, 7.18 dd (J$^3$ 7.75 Hz; J$^4$ 1.3 Hz, 1H) H (7); 4.12 s (3H) 8-methoxy H. |
| CCl$_3$ | H | Cl | 5Cl | 7Cl | 130–133 | 8.19 d (J$^4$ 2.1 Hz, 1H) and 7.72 d (J$^4$ 2.1 Hz; 1H) H (6 and 8); 8.16 s (1H) H (3). |
| CCl$_3$ | H | Cl | 6Cl | 8Cl | 102–104 | 8.19 s (1H) H (3); 8.15 d (1H) and 7.90 (1H) H (5 and 7). |
| CCl$_3$ | H | Cl | 5Cl | 8Cl | 123–124,5 | 8.23 s (1H) H (3); 7.83 d (J$^3$ 8.4 Hz; 1H) and 7.68 d (J$^3$ 8.4 Hz, 1H) H (6 and 7). |
| CCl$_3$ | H | Cl | 7Cl | 8Cl | 176–178 | 8.20 s (1H) H (3); 8.12 d (J$^3$ 9.0 Hz; 1H) and 7.77 d (J$^3$ 9.0 Hz; 1H) H (5 and 6). |
| CCl$_3$ | H | Cl | 5Cl | 8Me | 134–136 | 8.15 s (1H) H (3); 8.65 d (1H) and 7.55 d (1H) H (6 and 7); 280 s (3H) methyl (8). |

| R$^1$ | R$^6$ | X | R$^3$ | R$^2$ | m.p. (°C.) | $^1$H—NMR data (ppm) |
|---|---|---|---|---|---|---|
| CCl$_3$ | H | Cl | 6Cl | 8Me | 123–125 | 8.15 s (1H) H (3); 8.10 d (J$^4$ 2.0 Hz, 1H) H (5); 7.65 m (1H) H (7); 2.83 s (3H) methyl (8). |
| CCl$_3$ | H | Cl | 7Cl | 8Me | 138–139.5 | 8.13 s (1H) H (3); 8.05 d (J$^3$ 9.0 Hz; 1H) and 7.70 d (J$^3$ 9.0 Hz, 1H) H (5 and 7); 2.92 s (3H) methyl (8). |
| CCl$_3$ | H | Cl | 6Me | 8Cl | | 8.17 s (1H) H (3); 7.93 d (J$^4$ 1.8 Hz; 1H) H (5); 7.80 d (1.8 Hz, 1H) H (7); 2.60 s (3H) methyl (6) |
| CHCl$_2$ | H | Cl | 6Me | 8Cl | | 8.03 s (1H) H (3); 7.93 d (J$^4$ 1.8 Hz, 1H) H (5); 7.75 d (J$^4$ 1.8 Hz, 1H) H (7); 6.90 s (1H) 2-dichloromethyl H; 2.58 s (3H) 6-methyl. |
| CCl$_3$ | H | Cl | H | 6CCl$_3$ | 92–94 | 8.80-8.83 m (1H) H (5); 8.34-8.32 m (2H) H (7 and 8); 8.25 s (1H) H (3) |
| CCl$_3$ | H | Cl | H | 8CH$_2$Cl | 108–110 | 8.25 dd (J$^3$ 8.5 Hz; J$^4$ 1.5 Hz, 1H) and 8.03 d (b) (J$^3$ 7.0 Hz; 1H) H (5 and 7); 7.65 dd (J$^3$ 7.0 Hz; J$^{3'}$ 8.5 Hz 1H) H (6); 5.45 s (2H) 8-chloromethyl H. |
| CCl$_3$ | H | Cl | H | 8CHCl$_2$ | 95–97 | 8.45 dd (1H) and 8.35 dd (1H) H (5 and 7); 8.225 s (1H) and 8.22 s (1H) 3- and 8-dichloromethyl H; 7.85 dd (1H) H (6). |

-continued

| | | | | | |
|---|---|---|---|---|---|
| NMR data and melting point values of the compounds prepared according to the examples | | | | | |
| CCl3 | H | Cl | H | 8CCl3 | 134–136 | 8.58 dd ($J^3$ 7.5 Hz, $J^4$ 1Hz, 1H) and 8.44 dd ($J^3$ 9.0 Hz; $J^4$ 1.0 Hz, 1H) H (5 and 7); 8.24 s (1H) H (3); 7.75 dd ($J^3$ 9.0 Hz, $J^3$ 7.5 Hz; 1 H) H (6). |

Remarks

Melting points are disclosed without correction NMR spectra were taken in CDCl3 The decimal values were estimated. Tetramethylsilane was used as reference

Abbreviations s singlet
d doublet
t triplet
q quartet
m multiplet
b broad sign
$J^x$ coupling constant;
  x represents the bonds through which coupling is effected;
  heteronuclear coupling is indicated in sub-index e.g. F-H means fluoro-hydrogen coupling.

Antimicrobic Activity

The antimicrobic activity of the compounds of invention was tested in following microorganisms: *Bacillus subtilis, E. coli, Proteus vulgaris, Salmonella thyphi murium, Streptococcus faecalis, Staphylococcus aureus, Aspergillus niger, Aspergillus fumigatus, Candida albicans, Saccharomyces cerevisiae, Trichophyton mentagrophytes.*

2% bouillon solidified with agar-agar, and Sabouraud-glucosepepton were used as culture-medium.

The test compounds were dissolved in concentrated DMSO whereupon 0.1 ml of the solution was taken in the culture-medium cooled to a temperature of 40° C., the final pH of the culture medium was 7.4.

The dishes were inoculated with $10^6$ cells/ml, then incubated in a thermostat at 37° C. The evaluation was carried out on the third and seventh day. The cultures used for control were prepared at the same time quite identically as above but without any active agent.

Evaluation

A weak antifungoid activity was shown by the compounds of formula (I). The minimum inhibitory concentrations were measured between 300 and 500 μg/ml.

Antiphlogistic and Analgesic Activity

The antiphlogistic activity was measured by testing the inhibition of the paw oedema (Winter, C. A. et al. J. Pharmacol Exp. Ther 141 369 (1963)).

The analgesic effect was tested by the inhibition of writhing syndrome provoked by 3% acetic acid (Collier, H. et al. British J. Pharmacol. Chemother. 32, 295 (1968)).

The activity of acetylsalicylic acid and phenylbutazone were used as reference in above tests.

| Compounds of formula (I) wherein $R^1$ = CCl3; $R^6$ = H; X = Cl and | | Dose i.p. | Inhibition of carrageenan oedema (%) | Analgetic activity (%) |
|---|---|---|---|---|
| $R^2$ | $R^3$ | | | |
| 8-MeO | H | 100 | 65 | 100 |
| 8-Me | H | 100 | 61 | 60 |
| 8CCl3 | H | 100 | 50 | 60 |
| 5Cl | 8-Me | 100 | 47 | 100 |
| 6CF3 | H | 100 | 33 | 80 |
| 6MeO | H | 50 | 25 | 60 |
| 8CF3 | H | 100 | — | 40 |
| 6Me | H | 100 | — | 40 |
| 8CHCl2 | H | 100 | — | 40 |
| Acetylsalicylic acid | | 100 | 71 | 60 |
| Phenylbutazone | | 100 | 65 | 20 |

What is claimed is:

1. A chlorinated quinoline derivative of formula (I)

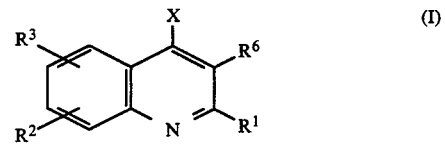

wherein
$R^1$ is —CCl3, —CF3, —CHCl2 or —CH2Cl,
$R^2$ is hydrogen when $R^3$ is not hydrogen, or is halogen, C1-4 alkoxy, C1-4 alkyl or $R^1$,
$R^3$ is hydrogen when $R^2$ is not hydrogen or is halogen, C1-4 alkyl, C1-4 alkoxy or CF3,
$R^6$ is hydrogen or halogen, and
X is halogen.

2. A compound of the Formula (I)

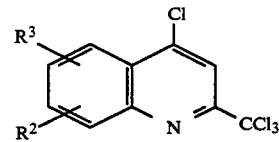

wherein
$R^2$ is halogen, C1-C4 alkoxy, C1-C4 alkyl, CCl3, CF3, CHCl2 or CH2Cl; and
$R^3$ is hydrogen or C1-C4 alkyl.

3. 2-trichloromethyl-8-methoxy-4-chloro-quinoline as defined in claim 2.

4. 2-trichloromethyl-8-methyl-4-chloro-quinoline as defined in claim 2.

5. 2,8-bis-trichloromethyl-4-chloro-quinoline as defined in claim 2.

6. 4,5-dichloro-2-trichloromethyl-8-methyl-quinoline as defined in claim 3.

7. 2-trichloromethyl-6-trifluoromethyl-4-chloro-quinoline as defined in claim 2.

8. 2-trichloromethyl-6-methoxy-4-chloro-quinoline as defined in claim 2.

9. 2-trichloromethyl-8-trifluoromethyl-4-chloro-quinoline as defined in claim 2.

10. 2-trichloromethyl-6-methyl-4-chloro-quinoline as defined in claim 2.

11. 2-trichloromethyl-8-dichloromethyl-4-chloro-quinoline as defined in claim 2.

12. A pharmaceutical composition which comprises as active ingredient a pharmaceutically effective amount of a compound of the Formula (I) as defined in claim 1 in admixture with a pharmaceutically acceptable inert carrier.

13. A pharmaceutical composition which comprises as active ingredient a pharmaceutically effective amount of a compound of the Formula (I) as defined in claim 2 in admixture with a pharmaceutically acceptable inert carrier.

14. An analgesic method of treatment which comprises the step of treating a susceptible subject with a therapeutically effective amount of the compound of the Formula (I) as defined in claim 1.

15. An antiphlogistic method of treatment which comprises the step of treating a susceptible subject with a therapeutically effective amount of the compound of the Formula (I) as defined in claim 1.

16. An antibacterial or antifungal method of treatment which comprises the step of treating a susceptible subject with a therapeutically effective amount of the compound of the Formula (I) as defined in claim 1.

* * * * *